(12) United States Patent
Korhonen et al.

(10) Patent No.: US 8,463,370 B2
(45) Date of Patent: Jun. 11, 2013

(54) METHOD AND APPARATUS BASED ON COMBINATION OF PHYSIOLOGICAL PARAMETERS FOR ASSESSMENT OF ANALGESIA DURING ANESTHESIA OR SEDATION

(75) Inventors: Ilkka Korhonen, Lempäälä (FI); Marcus Johannis Van Gils, Tampere (FI); Markku Paloheimo, Espoo (FI); Arvi Yli-Hankala, Tampere (FI); Matti Veli Tapani Huiku, Espoo (FI)

(73) Assignee: Instrumentarium Corporation (FI)

( * ) Notice: Subject to any disclaimer, the term of this patent is extended or adjusted under 35 U.S.C. 154(b) by 1483 days.

(21) Appl. No.: 12/052,542

(22) Filed: Mar. 20, 2008

(65) Prior Publication Data
US 2008/0167540 A1 Jul. 10, 2008

Related U.S. Application Data

(62) Division of application No. 10/614,749, filed on Jul. 7, 2003, now Pat. No. 7,367,949.

(51) Int. Cl.
*A61B 5/04* (2006.01)

(52) U.S. Cl.
USPC .......................................... 600/544

(58) Field of Classification Search
USPC ................................. 600/544, 545
See application file for complete search history.

(56) References Cited

U.S. PATENT DOCUMENTS

| 5,522,387 | A | 6/1996 | Simons |
| 5,699,808 | A | 12/1997 | John |
| 6,067,467 | A | 5/2000 | John |
| 6,117,075 | A | 9/2000 | Barnea |
| 6,126,595 | A | 10/2000 | Amano et al. |
| 6,315,736 | B1 | 11/2001 | Tsutsumi et al. |
| 6,338,713 | B1 | 1/2002 | Chamoun et al. |
| 6,361,501 | B1 | 3/2002 | Amano et al. |
| 6,685,649 | B2 | 2/2004 | Korhonen |
| 6,890,304 | B1 | 5/2005 | Amano et al. |

FOREIGN PATENT DOCUMENTS

WO 02/32305 A1 4/2002

OTHER PUBLICATIONS

Office Action issued by the European Patent Office in corresponding European Patent Application No. 04396042.6 dated Oct. 11, 2007.
European Search Report in corresponding European Patent Application No. 04396042.6 dated Oct. 27, 2004.
EEG, Heart Rate, Pulse Plethysmography and Movement Responses to Skin Incision, E. Seitsonen, et al., ASA Meeting Abstracts, Oct. 16, 2002, pp. 1-2.

*Primary Examiner* — Navin Natnithithadha
(74) *Attorney, Agent, or Firm* — Andrus, Sceales, Starke & Sawall, LLP

(57) ABSTRACT

The invention relates to a method for monitoring a condition of a patient under anesthesia or sedation, whereupon one, two, three or more signals are acquired, and the signal(s) represent(s) cardiovascular and/or combined electrical biopotential on skull activity of the patient. From said signal or signals are derived or calculated at least two parameter values related to a quantity like waveform amplitude, waveform periodicity, waveform morphology, waveform variability, energy, power, signal complexity and frequency content. A predetermined mathematical index for probability of patient comfort is used, in which function said parameters are variables, and successively changing probability index values of said mathematical index is calculated.

20 Claims, 8 Drawing Sheets

METHOD AND APPARATUS BASED ON COMBINATION OF PHYSIOLOGICAL PARAMETERS FOR ASSESSMENT OF ANALGESIA DURING ANESTHESIA OR SEDATION

CROSS-REFERENCE TO RELATED APPLICATION

The present application is a divisional of U.S. patent application Ser. No. 10/614,749, filed Jul. 7, 2003 now U.S Pat. No. 7,367,949, which is incorporated herein by reference.

FIELD OF THE INVENTION

The present invention relates to a method and an apparatus for monitoring a condition of a patient under anesthesia or sedation, while, in particular, information acquired from different sources in the patient is utilized.

BACKGROUND OF THE INVENTION

Concept of the depth of anesthesia has been of interest for recent decades, and several measures have been proposed to assess the depth of anesthesia. Recently, however, this unitary anesthesia theory of the existence of one-dimensional concept called "depth of anesthesia" has been strongly criticized as oversimplified. Instead it has been suggested that the anesthesia has not one but three main components: hypnosis, analgesia and muscle relaxation. Different anesthetic regimens have different effect on these three components. Furthermore, they have effects on both cortical and sub-cortical levels. An adequate anesthesia means unresponsiveness to both noxious and non-noxious stimuli. The former may be defined by means of hemodynamic, motor and endocrine stability, while the latter is related to the loss of consciousness and recall and amnesia. In practice the adequate anesthesia is administered by using a combination of drugs with different effects on brain, spinal cord, autonomic nervous system and neuromuscular junction. The combination of these effects hence creates the hypnotic, analgesic and muscle relaxing effects.

In general anesthesia the patient is conducted through the phases of anesthesia from the induction to the varying lengths of maintenance period and to the final emergence out from anesthesia. Though the patient does not usually recall any surgical events or perceive surgical pain, the recovery and the post-operative comfort of the patient very often depend on the quality of the anesthesia during the operation itself. Adequate administration of analgesic drugs—meaning that over-doses and under-doses can be avoided during anesthesia—is believed to advance the recovery of the patient. It has been suggested that this is due to two main reasons. Surgical pain may sensitize the pain pathways during surgery and thus lower the pain threshold in such a way that even rather intense pain management in the post-operative period is ineffective. It is said that the best way to avoid post-operative pain is a good and adequate administration of analgesics during operation. The other mechanism is probably related to the secretions of stress hormones during surgery. These hormones may have their effects long after surgery and can slow down the physical and psycho-physiological heeling of the patient. Adequate pain medications can suppress the autonomic nervous system and prevent excess secretion of these stress hormones. In this context the term "nociception" is commonly used to refer to the perception of pain. The receptors involved in pain detection are aptly enough referred to as nociceptors.

Nociceptive input is conveyed from the peripheral end organs to the central nervous system. Projection neurons in the spinal dorsal horn project to cell nuclei in supraspinal areas such as the thalamus, the brainstem, the midbrain etc. Of these, the synaptic junctions in the thalamus play a very important role in the integration and modulation of spinal nociceptive and non-nociceptive inputs. Nociceptive inputs are finally conducted to the cortex, where the sensation of pain is perceived. Stimulation of these central nervous system regions either electrically or chemically, e.g. by morphine and other opiates, produces analgesia in humans. Currently the anesthesia practices rely on rather subjective assessments of the adequacy of the drug treatment during anesthesia. Anesthesiologists observe the patient and decide for the proper drugs they give to the patient. Though this often is enough to avoid adverse events such as arousal or muscle movements during surgery, which in fact very seldom occur in normal anesthesia nowadays, more objective measures for the anesthesia are needed. Recently the progress in the biopotential signal analysis has lead in reasonable quantitative estimation of the hypnotic level of the patient, and thereby the titration of the anesthetic agents can be guided by these new measurements.

For instance, the neurological activity of the brain is reflected in biopotentials available on the surface of the brain and on the scalp. Thus, efforts to quantify the extent of anesthesia-induced hypnosis have turned to a study of these biopotentials. The biopotential electrical signals are usually obtained by a pair, or plurality of pairs, of electrodes placed on the patients scalp at locations designated by a recognized protocol and a set, or a plurality of sets or channels, of electrical signals are obtained from the electrodes. These signals are amplified and filtered. The recorded signals comprise an electroencephalogram or EEG, which normally has no obvious repetitive patterns, contrary to other biopotential signals, like electrocardiogram (ECG). Among the purposes of filtering is to remove electromyographic (EMG) signals from the EEG signal. EMG signals result from muscle activity of the patient and will appear in electroencephalographic electrodes applied to the forehead or scalp of the patient. They are usually considered artifacts with respect to the EEG signals. Since EMG signals characteristically have most of their energy in a frequency range from 40 Hz to 300 Hz, which is different than that of the EEG, major portions of the EMG signals can be separated from the contaminated EEG signal.

A macro characteristic of EEG signal patterns is the existence of broadly defined low frequency rhythms or waves occurring in certain frequency bands. Four such bands are recognized: Alpha waves are found during periods of wakefulness and may disappear entirely during sleep. The higher frequency Beta waves are recorded during periods of intense activation of the central nervous system. The lower frequency Theta and Delta waves reflect drowsiness and periods of deep sleep.

For clinical use, it is desirable to simplify the results of EEG signal analysis of the foregoing, and other types, into a workable parameter that can be used by an anesthesiologist in a clinical setting when attending the patient. Various such parameters for relating EEG signal data to the hypnotic state of the patient are discussed in the literature. Several use frequency domain power spectral analysis. These parameters include peak power frequency (PPF), median power frequency (MPF), and spectral edge frequency (SEF). A peak power frequency (PPF) parameter uses the frequency in a spectrum at which occurs the highest power in the sampled data as an indication of the depth of anesthesia. The median power frequency (MPF) parameter, as its name implies, uses the frequency that bisects the spectrum. In the same fashion, the spectral edge frequency uses the highest frequency in the EEG signal. To improve the consistency of an indicator of the hypnotic state or depth of anesthesia, several parameters are often employed in combination. For example, the spectral edge frequency (SEF) parameter may be combined with the time-domain burst suppression ratio (BSR) parameter to improve the consistency and accuracy with which the depth of anesthesia can be indicated. Also more complex combinations of parameters, like bispectral index (BIS) have been described.

There are a number of concepts and analytical techniques directed to the complex nature of random and unpredictable signals, like EEG. One such concept is entropy. Entropy, as a physical concept, describes the state of disorder of a physical system. Applying the concept of entropy to the brain, the premise is that when a person is awake, the mind is full of activity and hence the state of the brain is more nonlinear, complex, and noise like. Since EEG signals reflect the underlying state of brain activity, this is reflected in relatively more "randomness" or "complexity" in the EEG signal data, or, conversely, in a low level of "order." As a person falls asleep or is anesthetized, the brain function begins to lessen and becomes more orderly and regular. As the activity state of the brain changes, this is reflected in the EEG signals by a relative lowering of the "randomness" or "complexity" of the EEG signal data or conversely, increasing "order" in the signal data. When a person is awake, the EEG data signals will have higher entropy and when the person is asleep the EEG signal data will have a lower entropy.

According to the International Publication WO-02/32305 both the EEG and EMG signal data are typically obtained from the same set of electrodes applied, for example, to the forehead of the patient. The EEG signal component dominates the lower frequencies (up to about 30 Hz) contained in the biopotentials existing in the electrodes and EMG signal component dominates the higher frequencies (about 50 Hz and above). The presence of EMG signal can provide a rapid indication of the conscious-unconscious state of the patient. Importantly, because of the higher frequency of the EMG data signal, the sampling time can be significantly shorter than that required for the lower frequency EEG signal data. This allows the EMG data to be computed more frequently so that the overall diagnostic indicator can quickly indicate changes in the state of the patient. In one embodiment of the publication, the EEG signal data and the EMG signal data are separately analyzed and thereafter combined into a diagnostic index or indicator. As noted above, because of the celerity with which changes in the anesthetic state of the patient can be determined from the EMG data, the overall index can quickly inform the anesthesiologist of changes in the state of the patient.

Another way is to observe a photoplethysmographic (=PPG) signal, which is obtained by measuring the intensity of light transmitted through or reflected by the tissue. The dynamic part of the signal is caused by variations in blood volume and perfusion of the tissue, affecting scattering and absorption of the incident light. The most usual application of the signal is the measurement of the oxygen saturation of blood. The pulse waveform of the PPG signal is closely similar to that of the intra-arterial blood pressure. The waveform is reflecting the interaction between left ventricular output, i.e. cardiac output or stroke volume, and the capacitance of the vascular tree, also called vascular resistance. Blood pressure is determined by the cardiac output, which is stroke volume multiplied by heart rate, and vascular resistance. However, in addition to these global circulatory parameters, the dynamic capacitance of the vasculature affects also the nonlinear relationship of PPG signal and circulatory parameters. Especially complex is the relationship between the PPG waveform shape within one pulse and the integrated pulse-to-pulse variables. The PPG signal is related to the changes in peripheral tissue blood volume and blood absorptivity. As it is the blood flow, that causes the blood volume changes, the PPG signal is hence indirectly related to local blood flow. The flow, in turn, depends on the pressure gradient and local vascular dynamic resistance and capacitance.

The PPG measuring as such has been utilized for a long time. For instance U.S. Pat. No. 6,117,075 discloses a method and device for monitoring the depth of anesthesia (=DOA) during surgery by analyzing patterns and characteristics of oscillatory phenomena in measured pulse pressure and skin temperature signals. The method utilizes pulse pressure and skin temperature oscillatory patterns describe the nature of sympathetic vasomotor tone. The method monitors DOA in two ways. Spectral characteristics of skin temperature or pulse pressure oscillatory phenomena are used to describe the depth of anesthesia, and the concordance between oscillatory patterns of two physiological signals, which have been recorded simultaneously but at different locations, are used to describe the depth of anesthesia. According to the publication a PPG signal of an anesthetized patient is continuously monitored, and the recorded raw PPG signal is then processed so as to generate a signal depicting the beat-to-beat pulse pressure amplitude. Then the signal is derived by detecting peaks, and calculating the difference between each positive-negative peak pair, after which a further signal is processed in a manner so as to derive a data set describing very low frequency variations in pulse pressure over time in the 0.01-0.04 Hz range, that is, the PPG signal amplitude variability. Power spectrum analysis is finally performed on said further signal, and the received frequency power spectrum characteristics are used to describe the DOA, such that a progressively narrower bandwidth describe a progressively deeper level of anesthesia.

However, it appears that the position of the dicrotic notch as well as the PPG amplitude are dependent on various other sources than the status of vasoconstriction or vasodilatation, including fluid balance, temperature of the site of PPG measurement, heart rate, etc. Hence, these parameters may be interpreted with caution. Furthermore, they refer to the usage of the PPG information as a measure of the depth of anesthesia, which is an oversimplified one-dimensional assumption as described above.

The publication E. Seitsonen, M. van Gils, I. Korhonen, K Korttila, A. Yii-Hankala: "EEG, Heart Rate, Pulse Plethysmography and Movement Responses to Skin Incision"—A-582, 2002 ASA Meeting Abstracts, Oct. 16, 2002, discloses studies concerning evaluation of analgesia and nociception during general anesthesia. Raw EEG, the bispectral index, electrocardiography (ECG) and PPG data were collected and analyzed offline. RR-interval (RRI) tachogram was derived from ECG and frontal electromyography (FEMG) from EEG, and several beat-to-beat morphology parameters were derived from PPG signal, as well as various time and frequency domain parameters were computed from EEG, RRI and PPG data. When derived variables calculated as ratios or differences between post-incision and pre-incision values were compared, RRI, amplitude of the dicrotic notch in PPG, EEG spectral entropy and fEMG power appeared as primary variables in the optimal linear discriminant function between movers and non-movers. Finally it was concluded that combination of these parameters may be useful in assessing the level of analgesia and nociception during anesthesia. However, the publication does not provide any practical procedure for monitoring a patient.

U.S. Pat. No. 6,338,713, discloses a system and method for providing information to the user of a medical monitoring or diagnostic device to aid in the clinical decision making process. The preferred embodiment uses two estimators or predictors of the same physiological quantity, with each of the estimators being designed to detect specific states or artifacts in the estimated parameter and thus operating at a different point on its respective ROC curve; one chosen to provide high sensitivity, the other chosen to provide high specificity. The divergence between the estimators is indicated by the use of a shaded region between their respective time trends. The use of two estimators of the same parameters with different performance characteristics allows the system and method of the present invention to derive additional information about the underlying physiologic process over and above that which would be available from a single estimator. The system and method of the present invention can derive information from not only the instantaneous values of the estimators and the difference between them, but also from the time trend of the difference. Accordingly, this publication is primarily directed to the accuracy of a measurement, but does not discuss the problem how the level of analgesia could be reliably monitored while the patient is under anesthesia or sedation.

Anyway, the administration of analgetics is still largely based on the visual observations of the vital signs and the hemodynamic responses of the patient to surgical stimulation. Analgesic drugs are usually given, when the heart rate or blood pressure show fast increases or are in long term at the high end of the normal ranges. Different motoric responses, sweating and lacrimation of the patient can be observed as well. A further problem not considered in the publications is the possible suppressive effect of relaxants on at least some signals acquired from patient, which can have adverse effect on the reliability of the results received. The concept of analgesia is very complex and due to inter- and intraindividual variability the combined specificity and sensitivity for the single-parameter based methods is not very good.

Accordingly the main object of the invention is to achieve a method and apparatus for monitoring the anesthesia or sedation of a patient so that a reliable data about level or depth of analgesia would be available to an anesthetist or to other purposes.

The second object of the invention is to achieve a method and apparatus for monitoring the anesthesia or sedation capable of using measured signals derived from various sources of the patient, which means that the method should not be dependent on any single type of detector.

The third object of the invention is to achieve a method and apparatus for monitoring the anesthesia or sedation capable to deliver such results as an output, with the basis of which the adequacy of analgesia could be reliably enough assessed by inexperienced anesthetists or other operators, too.

The fourth object of the invention is to achieve a method and apparatus for monitoring the anesthesia or sedation functioning with an acceptable speed so that a change in analgesia to a hazardous direction is detected and reported early enough to allow timely corrective actions.

SUMMARY OF THE INVENTION

According to the first aspect of the invention the method for monitoring a condition of a patient under anesthesia or sedation, comprises the steps of: acquiring in real-time at least a first signal representing a cardiovascular activity of the patient; deriving, from said first signal, continuously at least a first and a second instantaneous parameter value related to a quantity selected from a group of quantities including waveform amplitudes, waveform periodicity, waveform morphology, and waveform variability; applying a predetermined mathematical index for probability of patient comfort, in which function said at least first and second parameters are variables; calculating successively changing values of said mathematical index; and indicating said successive index values.

In this case the first signal concerning cardiovascular activity is measured non-invasively using preferably photoplethysmography, though a pressure metering can be also used, whereupon the quantity for the first parameter value is a pulse wave amplitude, or a dicrotic notch height in the pulse wave, and the quantity for the second parameter value is a pulse rate, or a heart beat interval, or a temporal position of the dicrotic notch.

As an alternative, the method according to the invention comprises the steps of: acquiring in real-time at least a first signal and a second signal representing a cardiovascular activity of the patient; deriving, from said first signal and second signal, continuously at least a first and a third instantaneous parameter value related to a quantity selected from a group of quantities including waveform amplitudes, waveform periodicity, waveform morphology, and waveform variability; applying a predetermined mathematical index for probability of patient comfort, in which function said at least first and third parameters are variables; calculating successively changing values of said mathematical index; and indicating said successive index values.

In this case said first signal concerning cardiovascular activity is also preferably measured non-invasively using photoplethysmography, or measured using a pressure metering, whereupon the quantity for said first parameter value is a pulse wave amplitude, or a dicrotic notch height in the pulse wave. The second signal concerning cardiovascular activity is a cardiac excitation measured non-invasively using electrocardiogram, whereupon the quantity for said third parameter value is a heart rate of the electrical excitation.

As a further alternative, the method according to the invention comprises the steps of: acquiring in real-time at least a first signal and a third signal representing a cardiovascular and respectively a combined electrical biopotential on skull activity of the patient; deriving, from said first signal, continuously at least a first instantaneous parameter value related to a quantity selected from a group of quantities including waveform amplitude, waveform periodicity, waveform morphology, and waveform variability; calculating, from said third signal waveforms, continuously at least a fourth instantaneous parameter value related to a quantity selected from a group of quantities including energy, power, signal complexity and frequency content, each over a predetermined time period; applying a predetermined mathematical function for probability index of patient comfort, in which function said at least first and fourth parameters are variables; calculating successively changing values of said mathematical index; and indicating said successive index values.

In this case the first signal concerning cardiovascular activity is measured non-invasively using photoplethysmography, just as above, and the quantity for said first parameter value is a pulse wave amplitude, or a dicrotic notch height in the pulse wave. The third signal is a non-invasive measurement concerning neuromuscular and brain activity comprising electromyography and electroencephalogram. The electric myographic component is then extracted from said third signal, which originally is a combination of EMG and EEG, as an EMG partial signal and electro-encephalographic component as an EEG partial signal. Then the quantity for said fourth parameter value is a spectral power calculated from said EMG partial signal, and the quantity for said fourth parameter value is a subtraction of a response entropy, calculated from said third signal as a whole, and a state entropy, calculated from said EEG partial signal.

The first signal concerning cardiovascular activity can also be a cardiac excitation measured non-invasively using electrocardiogram, whereupon the quantity for the first parameter value is a heart rate or inter beat interval of the electrical excitation.

In the context of this alternative it is also possible, and prefarable as is now believed, to acquiring online a second signal representing a cardiovascular activity of the patient; deriving, from said and second signal, a third instantaneous parameter value related to a quantity selected from a group of quantities including waveform amplitudes, waveform periodicity, waveform morphology, and waveform variability; and introducing said at least third parameter in said predetermined mathematical function as an additional variable. Here the quantity for said first parameter value is a heart rate or inter beat interval of the electrical excitation.

In all cases the first and the second parameter values, or the first and the third parameter values, or the first and the fourth parameter values respectively are normalized on the basis their respective parameter values acquired continuously over a predetermined fixed time window including or excluding the latest real-time parameter value. The above mentioned parameter values for normalizing are acquired either from said patient prior to incision, or prior to intubation, or prior to starting anesthesia or sedation, or from a group of patients prior to or during incision and/or intubation and/or anesthesia or sedation. The mathematical index for probability is a non-linear equation, or a neural network algorithm, or a defined or fuzzy rule-based reasoning procedure.

The successively calculated value or values is/are indicated or informed or made available to the operating person or persons for further actions, and/or possibly indicated or informed or made available to an additional apparatus for further processing. It shall be noted that the absolute value of the probability index according to the invention is the most valid data made available to the personnel, though a change of the index may increase informativeness, too.

According to the second aspect of the invention the apparatus for monitoring a condition of a patient under anesthesia or sedation, comprises at least first sensor means for online receiving substantially continuous electrical signal representing a cardiovascular activity of the patient; first time measuring means and a first voltage/current dependent circuit connected with said sensor means; first memory means storing criteria of predetermined pulse wave parameters to be extracted from said signal; first deriving means connected to said first memory means, said first time measuring means and said first voltage/current dependent circuit for continuously extracting first and second values of said predefined pulse wave parameters; second calculation means for successively performing a predetermined mathematical program having temporally variable probability index values, based on said first and second pulse wave parameter values, as an output; and a display and/or connections into further devices.

As an alternative, the apparatus according to the invention comprises at least first and second sensor means for online receiving substantially continuous electrical signals representing a cardiovascular activity of the patient; first and second time measuring means and a first and second voltage/current dependent circuit connected with said sensor means; first memory means storing criteria of predetermined pulse wave parameters to be extracted from said signals; first deriving means connected to said first memory means, said first time measuring means and said first voltage/current dependent circuit for continuously extracting first values of said predefined pulse wave parameters; second deriving means connected to said first memory means, said second time measuring means and said second voltage/current dependent circuit for continuously extracting third values of said predefined pulse wave parameters; second calculation means for successively performing a predetermined mathematical program having temporally variable probability index values, based on said first and third pulse wave parameter values, as an output; and a display and/or connections into further devices.

As a further alternative, the method according to the invention comprises at least first and third sensor means for online receiving substantially continuous electrical signals representing a cardiovascular activity and respectively an electrical biopotential activity of the patient; first and third time measuring means and a first and third voltage/current dependent circuit connected with said sensor means; first memory means storing criteria of predetermined parameters to be extracted from said signals; first deriving means connected to said first memory means, said first time measuring means and said first voltage/current dependent circuit for continuously extracting first values of predetermined pulse wave parameters; first calculation means connected to said first memory means, said third time measuring means and said third voltage/current dependent circuit for continuously extracting fourth values of predetermined biopotential parameters; second calculation means for successively performing a predetermined mathematical program having temporally variable probability index values, based on said first and fourth parameter values, as an output; and a display and/or connections into further devices.

Generally speaking, at least one height or amplitude parameter, i.e. parameter in y-direction in an orthogonal coordination, is derived or calculated from the signal or signals for usage in the function of probability according to the invention, and at least one time or temporal parameter, i.e. parameter in x-direction in an orthogonal coordination, is also derived or calculated from the signal or signals for usage in the function of probability according to the invention. In this context the entropy parameter is considered to a height or amplitude parameter.

The main advantage of the method as compared to the state-of-art is that by the method it is possible to significantly increase the specificity of analgesia monitoring as compared to a usage of a single variable as an input. The method is also practical in the sense that it is based on the new usage of the signals which are either routinely monitored during anesthesia, or which may be easily monitored with the existing patient monitors, e.g PPG, EEG etc., and hence the method does not require expensive new sensors or monitoring means to be attached to the patient.

By combining information from various sources each related to level of analgesia but alone providing insufficient sensitivity and/or specificity for analgesia assessment in practice, it is possible to improve the quality of analgesia level monitoring. The most potential input signals comprise heart rate (as measured from ECG, pulse plethysmography, blood pressure or some other signal related to functioning of heart and providing beat-to-beat rhythm of the heart), plethysmographic pulse parameters (for example plethysmographic pulse notch position information) and frontal electromyography signal (fEMG).

BRIEF DESCRIPTION OF THE DRAWINGS

FIG. 5D provides annotations related to surgical procedures.

DETAILED DESCRIPTION OF THE PREFERRED EMBODIMENTS

Figure 1:
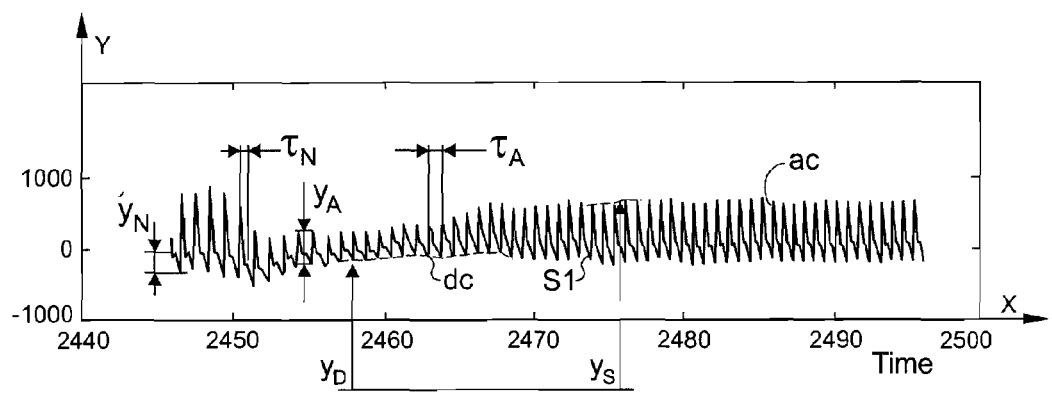
FIG. 1 shows an example of a typical non-invasive PPG signal, or non-invasive or invasive blood pressure metering signal, representing cardiovascular pulse wave or blood pressure of a patient, which signal can be used as a starting raw signal in the invention.

In the first embodiment of the invention the combination of the parameter values used in the probability function P for the patient comfort in anesthesia are obtained only from one cardiovascular signal S1. Though the outmost simplicity of this method in practice, multiple of quantities can be derived in the way that they still carry different type of information from the function of the autonomic nervous system (=ANS). The heart rate and its variability, which mainly reflects the parasympathetic activity, can be extracted from the periodicity of the measured pulse wave, i.e. from the beat-to-beat pulse rate. On the other hand the amplitude of the pulse wave, especially when measured in peripheral tissue, carries information from the skin circulation, which is mainly controlled by the sympathetically branch of ANS. In case when the parasympathetical activity of the patient is stronger than the sympathetical activity, the heart rate is low, blood pressure is normal and peripheral circulation works normally as the blood vessels are dilated. If the patient has pain or is uncomfortable, the heart rate is higher and blood vessels are more constricted, which results in smaller peripheral pulse wave amplitudes, especially in the plethysmographic wave. These signs of excess sympathetical activity result also in elevated blood pressures easily measured by continuous blood pressure meters. In summary, the sympathetical activation, which increases heart rate, induces vasoconstriction in the peripheral circulation and increases blood pressure, is an indication of patient discomfort. Usually this appears as a sudden change in the plethysmography waveform parameters and blood pressure. On the other hand the low activity of the sympathetical and parasympathetical branch of ANS and the balance between these regulation mechanisms is an indicator of adequate patient comfort. Accordingly, it can be understood that even one signal can carry quite a detailed information from the state of the autonomic nervous system and from the patient comfort.

In the simplest embodiment only oxygen saturation measurement with the pulse wave signal (PPG) is enough to calculate the probability index of patient comfort. As saturation measurement is in practice compulsory in anesthesia this advantageous embodiment of the invention is almost always available to all patients.

In the second embodiment of the invention the combination of the parameter values used in the probability function P for the patient comfort in anesthesia are obtained only from two cardiovascular signals S1 and S2. The heart rate is extracted from the ECG waveform instead of the pulse wave of the photoplethysmographic or blood pressure measurement. This is advantageous, because the heart beat interval can be determined more accurately, and more detailed information can be extracted especially from the parasympathetical activity and from the parasympathetical—sympathetical balance of ANS. The better precision of the beat-to-beat interval is due to typically higher sampling frequencies of the ECG measurement and more importantly due to the fact that the R-peak in the ECG waveform is very much sharper than the pulse wave peak. When the signal quality in PPG, due to poor blood circulation, is bad or when the PPG or BP waves are extremely round, the exact beat interval can still be determined with precision from the ECG waveform. As the precision of the determination of the R-R interval from ECG—even without poor patient condition—is always very good, more parameters, e.g. heart rate variability (HRV), can be extracted from the temporal cardiac function. These improve the performance of the probability index for the patient comfort and leads into better sensitivity and specificity of the index.

In the third embodiment of the invention the combination of the parameter values used in the probability function P for the patient comfort in anesthesia are obtained only from a cardiovascular signal S1 and a biopotential signal S3 on skull or scalp. This is one of the preferred embodiments, together with the embodiment utilizing three signals S1, S2 and S3, regarding the specificity and sensitivity of combining parameters into one index of patient comfort, is achieved with the biopotential measurement on patient skull. The cardiovascular measurement are good indicators, but sometimes too unspecific to patient comfort as they are influenced by other psychological emotional triggers or by physiologic factors such as the intra-vascular volume status of the patient, by sepsis, arrhythmias, respiratory disturbance or hypertension. Therefore, in addition to the cardiovascular quantities, information is needed from the brain activity, its psychophysiological aspects and from the overall state of the central nervous system. By biopotential measurement on skull, including electroencephalography, electromyography and skin conductivity measurement, one can derive information, which is specific to the cortical brain activity and hypnosis, to the facial muscle nerve activity and to the sudomotor (sweating) activity, respectively. Hypnosis describes the state of human cortex, especially various states of consciousness and unconsciousness, i.e. ability of cortical processing of the sensory nerve information. Facial muscle nerve activity describes the motoric control of these muscles (from cortex), but also unintentional facial expressions, which originate from the brain stem level and reflect also the state of the autonomic nervous system or the state of the central nervous system at the subcortical level. Finally the sudomotor activity is emotionally triggered from the cortex, but as the facial 'mimic' muscles, its activation is often a result of painful or discomfortable stimulation without real perception of pain at the cortical level. It is well known that discomfort increases sweating—during anesthesia it is a common practice to sense the patient forehead for sweating, which among anesthesiologist is often interpreted as a sign of discomfort even in deep hypnosis. It is believed that both the sudomotor and electromyographic activity are specific indicators of the sympathetical activation and patient discomfort and that the cortical activity is an additional parameter for the overall suppression in the central nervous system. All this information is complementary within itself, but in combination with the cardiovascular signals, it forms an entity, by which the patient discomfort and comfort can be estimated even in deep hypnosis. Even more than that, the index of hypnosis and the index of analgesia can be made rather orthogonal to each other. This means that the indices are independent and that the anesthesiologist can make specific decision about whether patient needs more analgesic or hypnotic drugs.

If the biopotential measurement is arranged on the forehead of the patient, both the facial muscle (fEMG) and brain (EEG) activity components are present in the raw measured signal S3. In principle, the same arrangement is suitable to measure the skin contact of the electrodes with the scalp, in which the sweating of the forehead is as well seen. We, however, omit this contribution and concentrate on the signal with EEG and fEMG, only. We also limit our discussion to one of the advantageous embodiment of the invention, namely to a technique of spectral signal entropy, the concept of which can be applied to both EEG and fEMG signal components.

Entropy, when considered as a physical concept, is proportional to the logarithm of the number of microstates available to a thermodynamic system, and is thus related to the amount of "disorder" in the system. In this context, entropy describes the irregularity, complexity, or unpredictability characteristics of a signal. In a simple example, a signal in which sequential values are alternately of one fixed magnitude and then of another fixed magnitude has an entropy value of zero, i.e. the signal is completely regular and totally predictable. A signal in which sequential values are generated by a random number generator has greater complexity and higher entropy. Entropy is an intuitive parameter in the sense that one can visually distinguish a regular signal from an irregular one. Entropy also has the property that it is independent of absolute scales such as the amplitude or the frequency of the signal: a simple sine wave is perfectly regular whether it is fast or slow. In an EEG application, this is a significant property, as it is well known that there are interindividual variations in the absolute frequencies of the EEG rhythms.

There are various ways to compute the entropy of a signal. In frequency domain, spectral entropy may be computed in ways generally known. The starting point of the computations is the spectrum of the signal. Such an algorithm is implemented in the Datex-Ohmeda Entropy® Module, in which the discrete Fourier transformation of the signal is calculated. A flat spectrum indicates a high and peaky spectrum a low entropy value. Without going into more details, we next describe how the physical concept of spectral entropy is employed in clinical decision making about the patient comfort.

Figure 4:
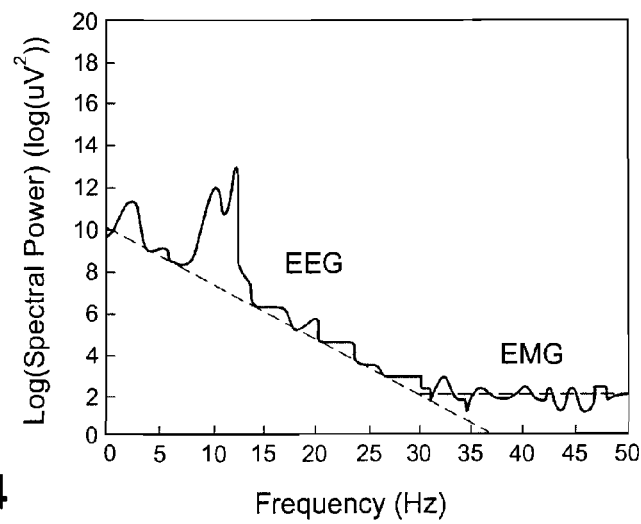
FIG. 4 shows a typical power spectrum of a biopotential signal EEG+EMG.

Referring to FIG. 4, it is informative to consider two entropy indicators, one over the EEG dominant frequency range alone and another over the complete range of frequencies, including both EEG and EMG components. The State Entropy (SE) is computed over the frequency range from 0.8 Hz to 32 Hz. It includes the EEG-dominant part of the spectrum, and therefore primarily reflects the cortical state of the patient. The Response Entropy (RE) is computed over a frequency range from 0.8 Hz to 47 Hz. It includes both the EEG-dominant and EMG-dominant part of the spectrum. It is advantageous to normalize these two entropy parameters in such a way that RE becomes equal to SE when the EMG power, i.e. sum of spectral power between 32 Hz and 47 Hz, is equal to zero, as the RE-SE-difference then serves as an indicator for EMG activation. Consequently, RE varies from 0 to 1, whereas SE is always smaller than 1. When there is EMG activity, spectral components within the range 32-47 Hz differ significantly from zero and RE is larger than SE. With these definitions, SE and RE both serve their own informative purposes for the anesthesiologists. The State Entropy is a quantity which is stable enough to provide the anesthesiologist at one glance of the number an idea of the current cortical state the patient is in. The Response Entropy, on the other hand, reacts fast to changes as it can be calculated using shorter time windows than SE.

There are several parameters that could be classified as describing waveform morphology, including at least: the area under the pulse, FWHM (=full width at half maximum value of the pulse), amplitude/period, dicrotic notch height in absolute units, dicrotic notch height in relative units (=height/amplitude), skewness of the pulse, any characteristics after derivation or multiple of derivations of the signal, any parameter after FFT analysis (=first harmonic peak/base frequency peak, etc), any signal processing or modelling parameter (=e.g. AutoRegressive-model of the signal). In this context the parameters that could be classified as describing waveform amplitude include: the relative and absolute difference between the peak value and the minimum value of the pulse wave. It is especially pointed out that here the "wave" includes a bias, generally called as a dc-component of the signal, which variates considerably slower than the pulse, i.e. the ac-component of the signal. Accordingly, there is pulsation of the signal and a level of the signal, around which level said pulsation occurs. There are some parameters that could be classified as describing waveform periodicity, including at least: pulse rate, heart rate, heart beat interval, temporal position of the dicrotic notch in absolute units (after the peak-position or after any fixed position in one single pulse) or in relative units (=temporal position/period), P-R interval, Q-T interval, QRS duration. There are a plurality of parameters that could be classified as describing waveform variability (=changes of any waveform characteristics with time), including at least: SD (=standard deviation over a fixed time window), SSD (=SD of the successive signal points=SD after derivation of the signal), RMS-value (as above), LF (=low frequency variability of any waveform characteristics: is related with the sympathetical activity of ANS), HF(=high frequency variability of any waveform characteristics: is related with the parasympathetical activity of ANS), Entropy of any characteristics (measure of disorder, see Spectral entropy of EEG). It is also noted here that non-stationarity of the signal is one cause for waveform variability and the indices and methods, by which the non-stationarities are detected, produce variables, which shall be interpreted as waveform variability. Non-stationarity here is any statistically significant temporal deviation of statistical measures of the signal from the average values. As to the signal complexity, there are at least the following parameters: Spectral entropy, approximate entropy, Lempel-Ziv Complexity, Golmogorov-Sinai entropy, Fractal exponents, bispectral indices, correlation lengths (in time). At least the following parameters can be classified in frequency content: FFT spectrum derived parameters like spectral entropy, power at different brain rhythm bands, median frequency, spectral edge frequency, 95% power edge frequency, mean frequency, peak amplitude frequency (=highest power frequency). The power and energy are self-explanatory parameters, and does not need farther explanation.

Figure 2:
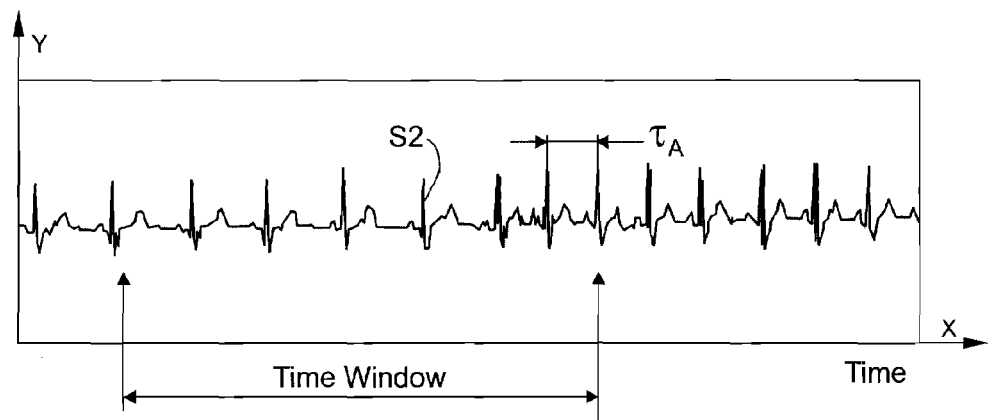
FIG. 2 shows an example of a typical non-invasive ECG signal representing cardiac excitation of a patient, which signal can be used as a starting raw signal in the invention.
Figure 3:
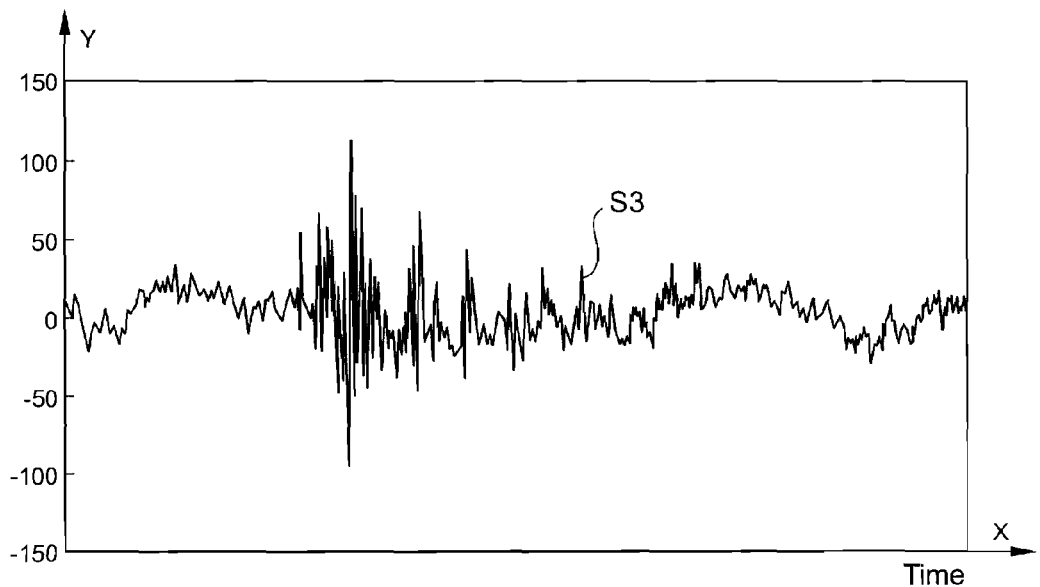
FIG. 3 shows an example of a typical non-invasive EEG+EMG signal representing a combination of brain activity and neuromuscular activity of a patient, i.e. biopotentials, which signal can be used as a starting raw signal in the invention.

In the FIGS. 1 to 3 the following parameters, which are the most frequently used and preferred parameters, are visualized: pulse wave amplitude $y_A$; dicrotic notch height $y_N$ in the pulse wave; heart beat interval $\tau_A$, temporal position of the dicrotic notch $\tau_N$; systolic blood pressure $Y_S$; and diastolic blood pressure $Y_D$. The entropies, which are frequently used and preferred parameters, too, cannot be visualized. The parameters listed above are all familiar to a person skilled in the art so that it is not necessary to mark them in the figures.

The normalizing discussed above means that the prevailing or present or latest parameter value is subtracted from the calculated average value of the historical parameter values, or vice versa, or the prevailing or present or latest parameter value is divided by the calculated average value of the historical parameter values, or vice versa. One of these, two of these, or three of these, or all of these can be used simultaneously in the predetermined mathematical function according to the invention. The average value can be a constant average value over time period, or over a number of heart beat pulses, or a moving weighted or non-weighted average value over a time period or over a number of heart beat pulses during operation of the patient, or a constant group average over certain patient type(s).

The mathematical index for probability can be generally formed, according to the invention, several ways. Also the history data, i.e. the parameter values acquired continuously over a predetermined fixed time window including or excluding the latest real-time or prevailing parameter value, can be processed several ways. The probability index of the invention combines in real-time the historical parameter values with the prevailing parameter data from at least two sources. The index P or P(t) for probability of patient comfort is a function, which shall be understood to be either an equation, or an algorithm, or a reasoning or logical procedure, in which at least two parameters are variables This mathematical combination may be done by using some nonlinear equation, logical rules and/or operators, artificial neural networks, fuzzy logic, etc.

The index of patient comfort may be calculated by the following nonlinear equation:

$$P(t) = \frac{1}{1 + e^{-(aX(t)+bY(t)+cZ(t)+d)}}$$

where
P is the index for probability of patient comfort,
a, b, c, d are parameters selected to optimise the performance of the index,
X(t), Y(t), Z(t) are monitored current values of the normalized parameter values,
t is the sample time.

It should be noted that the coefficients of the mathematical equation must be selected according to the quantities and parameters used and according to the available signal, and will depend on the exact choice and implementation of the monitored ensamble of parameter history values and their normalization means.

The index of patient comfort may be also determined by using rule-based reasoning. These rules are by translating clinical knowledge acquired in our experimental studies on nociception into formal "if . . . then . . . else" statements that can be directly implemented into a computer programming language. The probability index P is then calculated as a sequence of reasoning statements. It is possible to use exactly defined rules as well as fuzzy rules in the reasoning. The value ranges of the parameters as well as the index for probability are in this case discredited into certain intervals to allow for symbolic reasoning. For example the index P can be subdivided into three or more intervals; if $0 \leq P \leq 0.3 \rightarrow P$ is labeled as having "low" value, if $0.3 < P \leq 0.7 \rightarrow P$ is labeled as having "medium" value, and if $0.7 < P \leq 1.0 \rightarrow P$ is labeled as having "high" value. Similar divisions could be done for the monitored values X(t), Y(t), Z(t). For example:

```
if ((X(t) = "high") or (X(t) = "medium")) then
    P(t) := "low"
else
    if ((Y(t) = "low") and (Z(t) = "high")) then
        P(t) := "high"
    else
        P(t) := "medium"
``` where
=comparison operator (test of equality),
:=assignment operator (the value of the operand on the right hand side is assigned to the operand on the left hand side).

This example indicates that when X(t) has a medium or high value then the probability of nociception P is low. If X(t) has a low value and Y(t) is low and Z(t) has a high value then P is high. In other cases P is medium.

Further, the index of patient comfort may be also determined by using previously recorded data that has been labeled at each time instance with an indication of whether there was nociception or not, e.g., annotated by an anesthetist. This kind of procedure can be called neural network. Typical examples cases of X(t), Y(t), and Z(t) as recorded during instances of nociception and non-nociception can then be constructed. This can be done by grouping vectors v(t) =(X(t), Y(t), Z(t)) that have been measured during nociception periods together into a set of i "typical" nociception examples, {vi}, and grouping vectors of data that have been measured during non-nociception periods into a set of j typical non-nociception examples, {wj}. This grouping can be implemented with various different algorithms, e.g., averaging, self-organisation. Once we have constructed these sets we can use them to estimate a value of p(t) for data values recorded at t.

For data samples X(t), Y(t), Z(t) monitored at time t the vector u(t) =(X(t), Y(t),Z(t)) is constructed.

The distances D between u(t) and each element of {vi} and {wj} are calculated. This gives i+j distance calculations (as distance measure e.g., the Euclidean distance can be used).

The smallest distance calculation result is noted.

If this smallest distance was obtained when comparing u(t) with an element of {vi} then P(t) is assigned as being "high", if it was obtaining when comparing with an element of {wj} then P(t) is assigned as being "low".

It is also possible to use more than those two parameters described above. Accordingly, it is possible add measurement of another type cardiovascular activity in the first embodiment of the invention so that there are two signals and three parameter values for calculation of the probability index. In the second embodiment of the invention it is possible to derive a further parameter from the two signals so that there are three parameter values for calculation of the probability index. In the third embodiment of the invention it is possible to derive a further parameter from the two signals so that there are three parameter values for calculation of the probability index, too. It shall be understood that it is also possible to perform further online measurements, whereupon three signals are acquired, and three or four or more parameters are included in the calculation of the probability index.

EXAMPLE

Figure 5A:
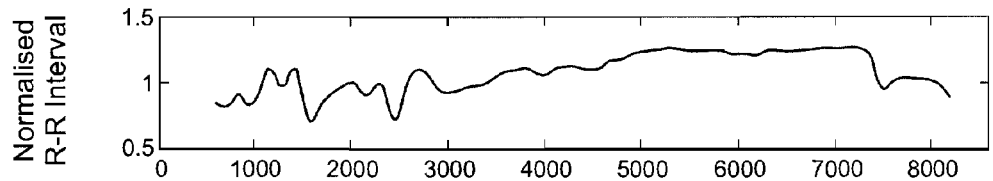
FIGS. 5A-5D are an example of real data recorded from a patient representing the intermediate results and final probability index calculated according to the invention.
Figure 5B:
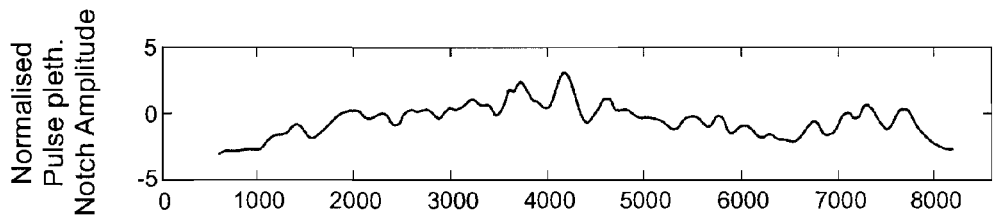
Figure 5C:
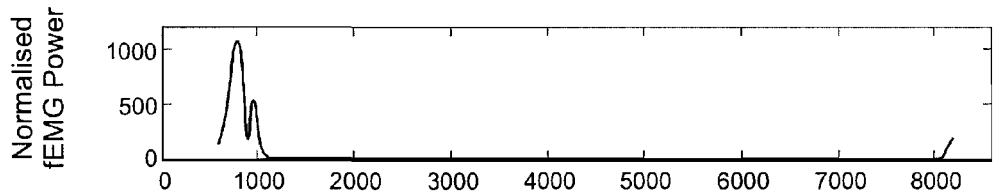
Figure 5D:
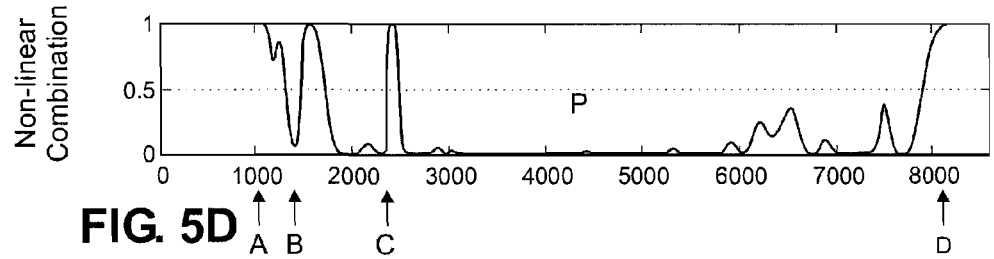
Figure 6:
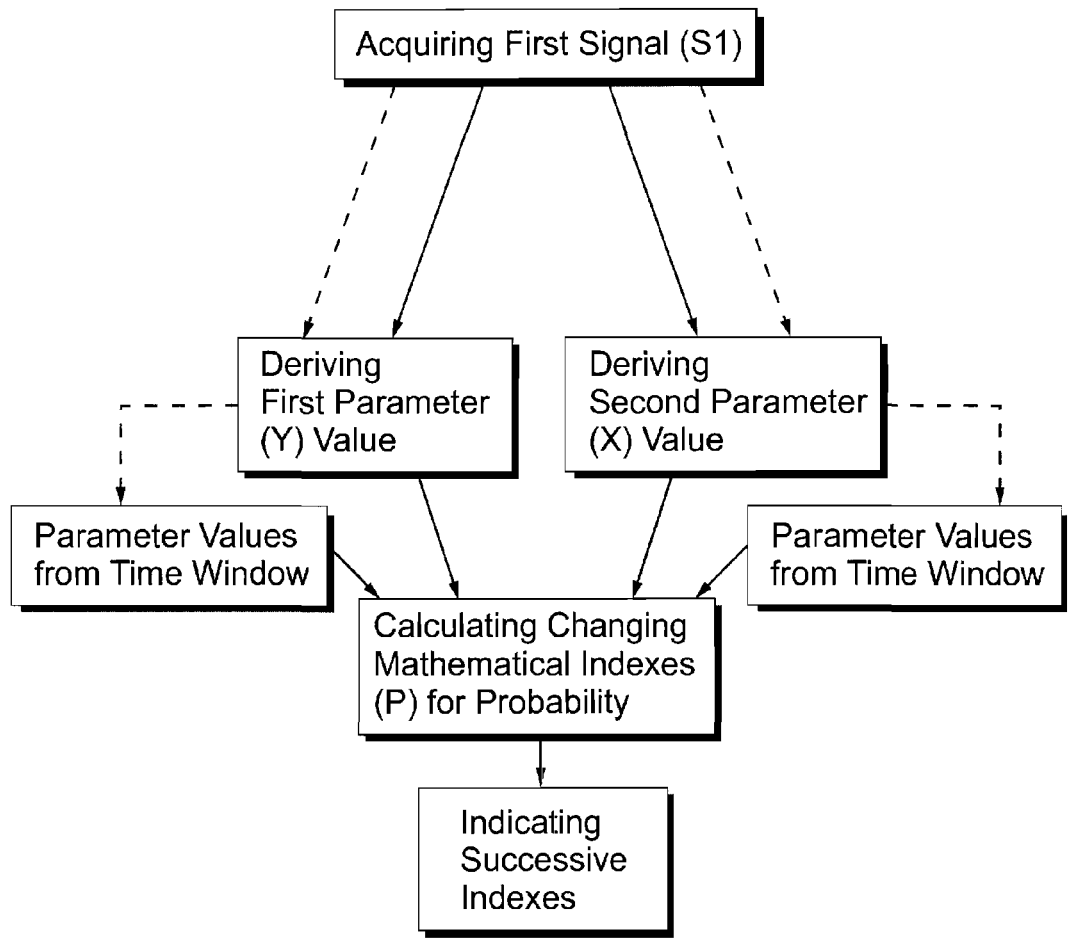
FIGS. 6-8 show the main steps of the preferred first, second and third embodiment, respectively, of the invention for processing the signal acquired from a patient.
Figure 7:
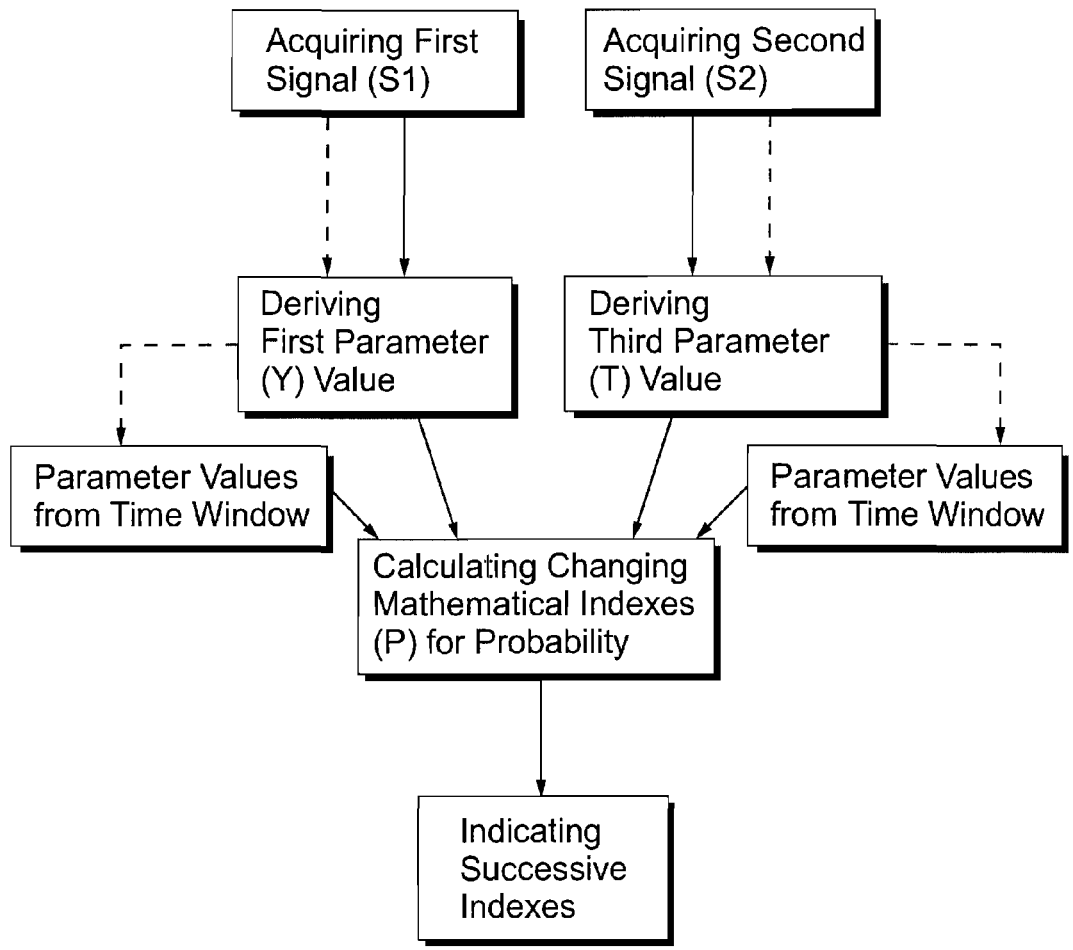
Figure 8:
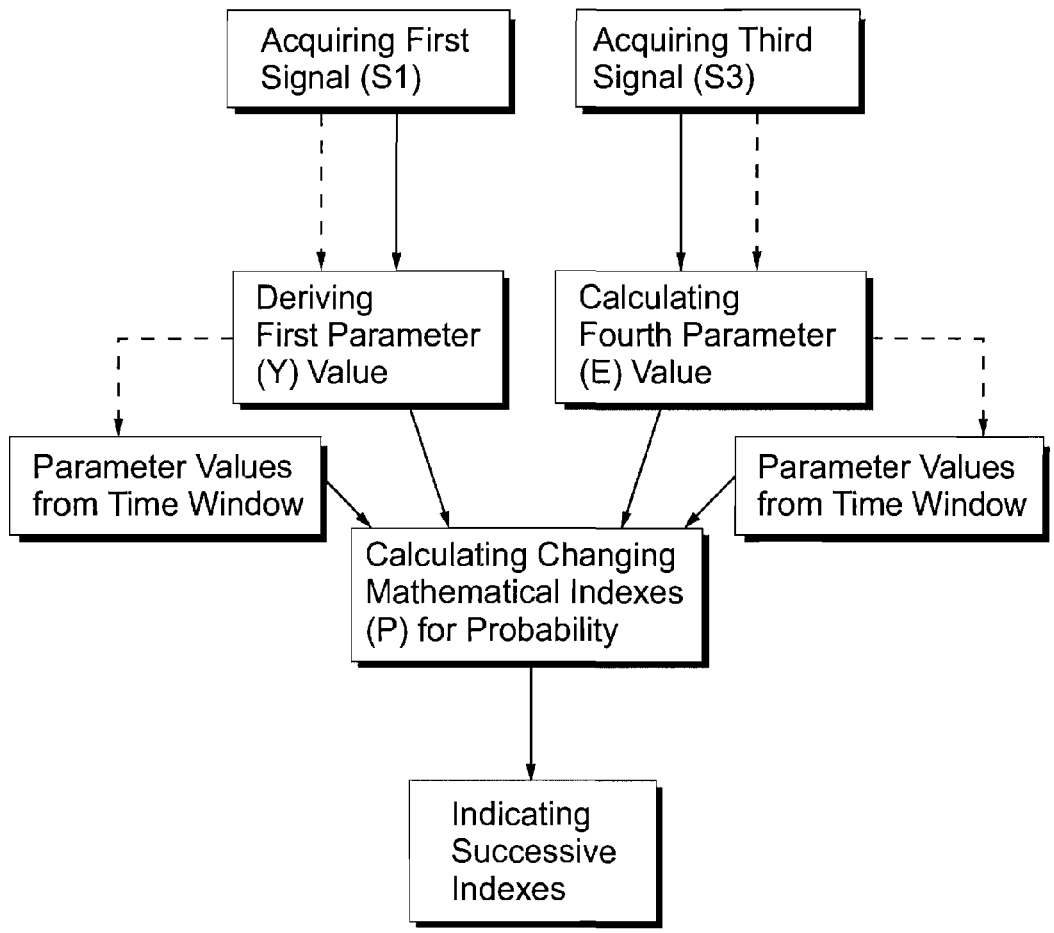
Figure 9:
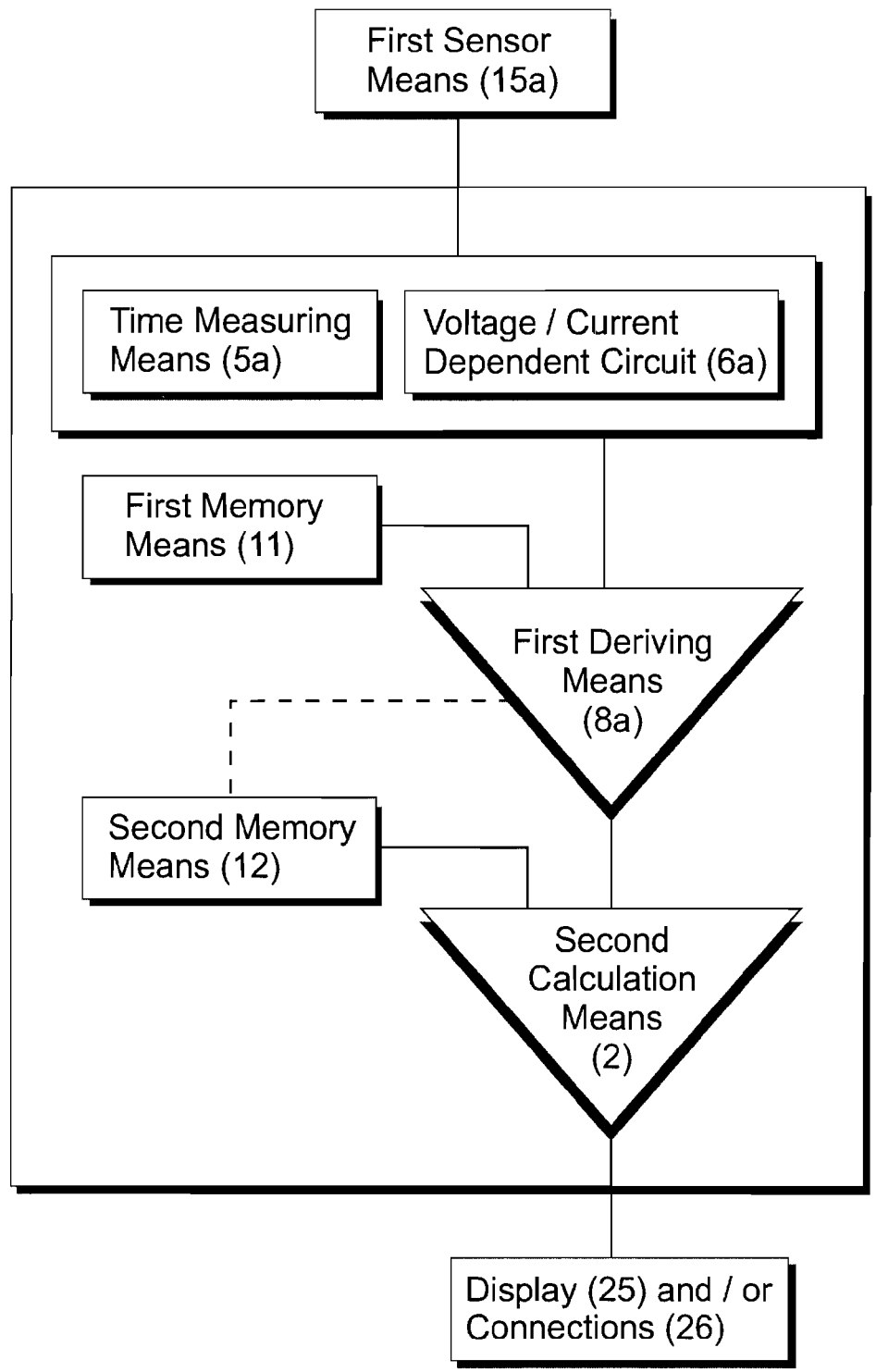
FIGS. 9-11 show the main components of the preferred first, second and third embodiment, respectively, of the invention as flow chart. The components shown can be separate electronic units, but quite as well portions of a computer program or programs for microprocessors.
Figure 10:
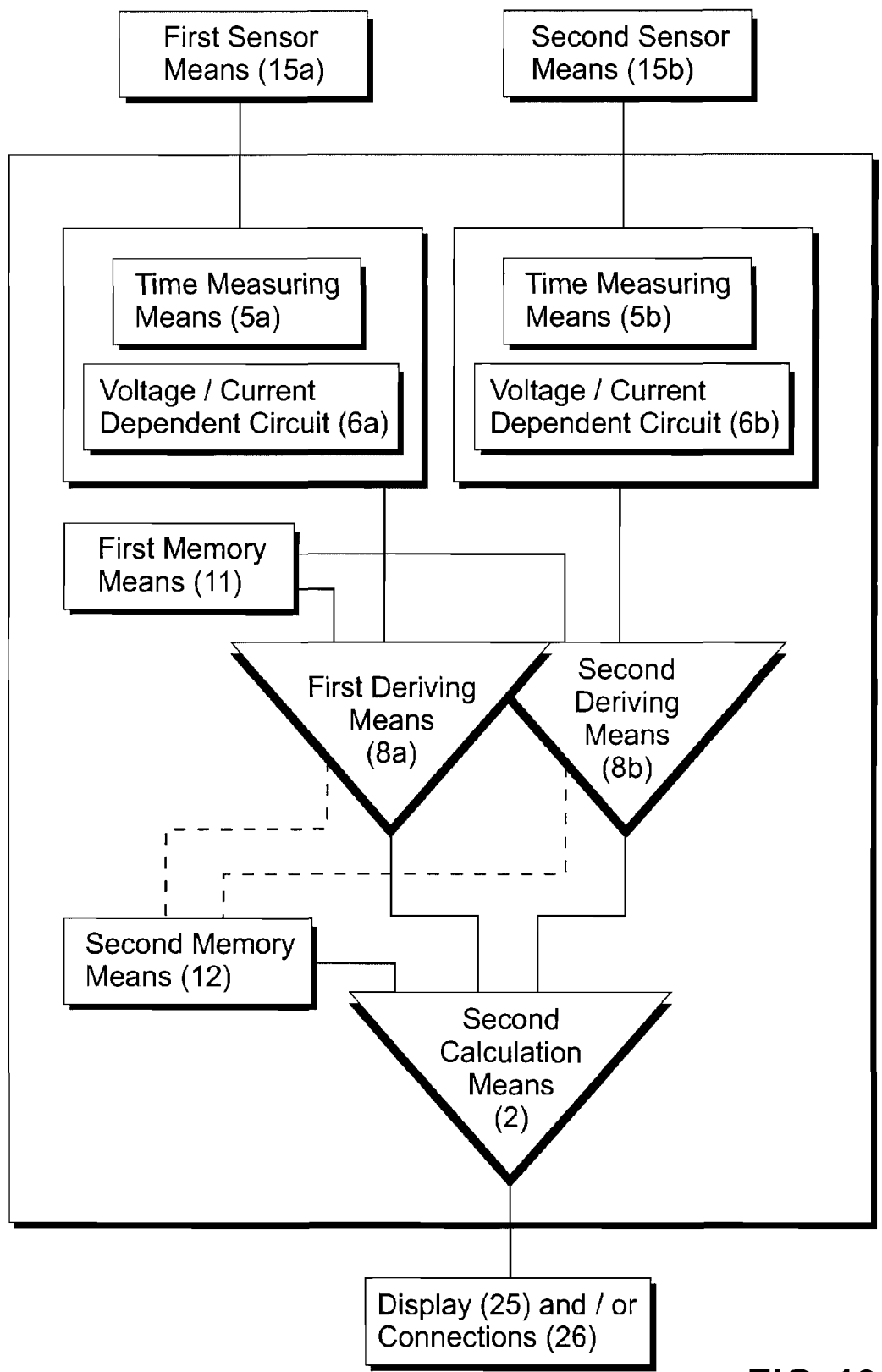
Figure 11:
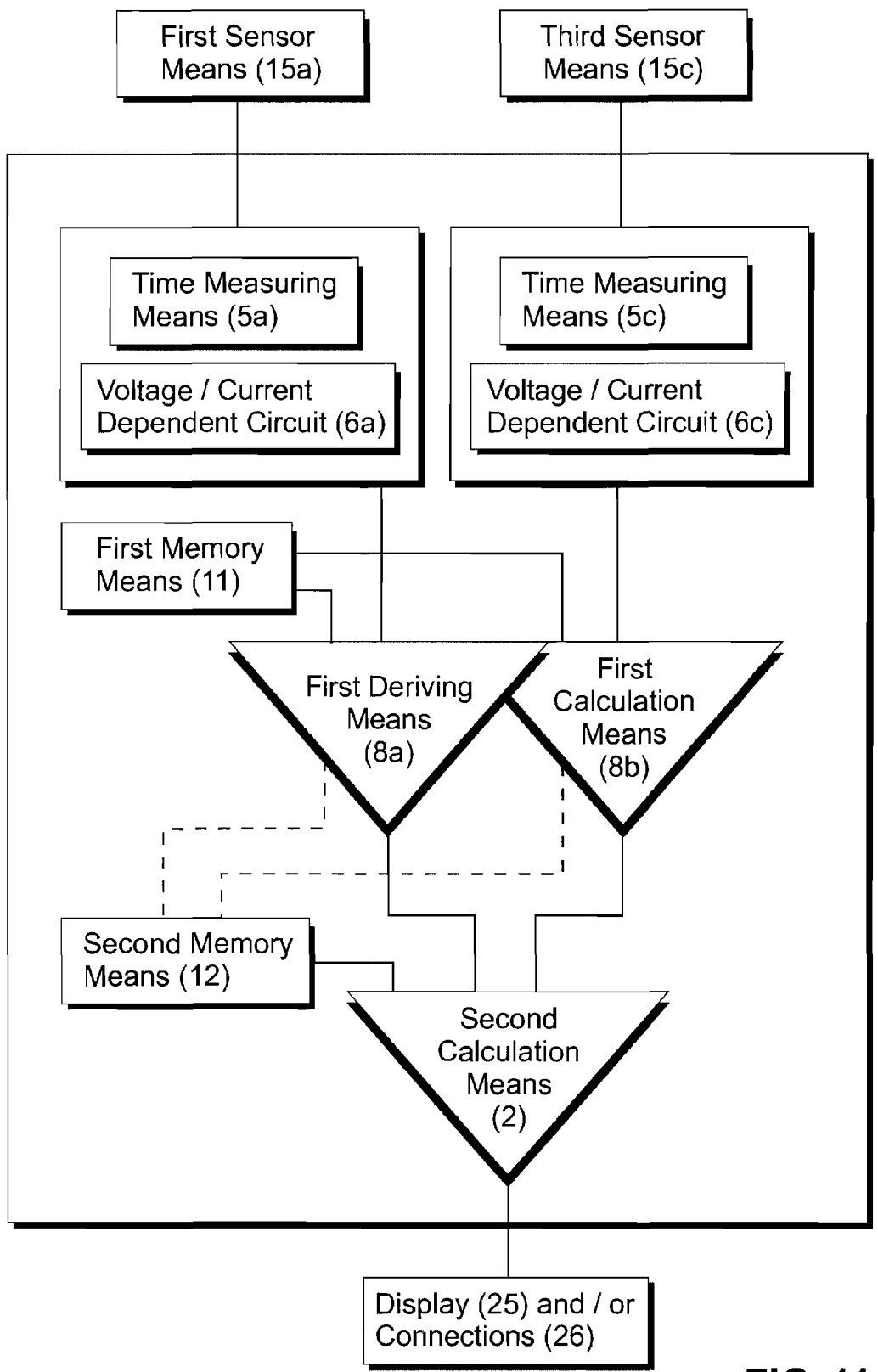

In the following an example is described, which is based on an unpublished material concerning 23 patients, single-variable based estimators based on a PPG-signal, and a fEMG-signal for the level of analgesia could classify the patients' responses to skin incision with 65-74% correctness i.e. the physiological responses could discriminate the patients who moved or did not move as a response to skin incision. When the information in these variables is combined the correctness for detection of insufficient analgesia is improved to 83%. In the example of real-time data were recorded during abdominal hysterectomy surgery. After induction (FIG. 5D: Arrow A) with fentanyl 1 μg/kg iv and propofol 1 mg/kg iv anesthesia was deepened with sevoflurane 8% in 100% oxygen via facial mask until endotracheal intubation (FIG. SD: Arrow B). Sevoflurane concentration was adjusted to equal 0.8 MAC (1.6% end-tidal). Surgery began 14 min after intubation with skin incision (FIG. 5D: Arrow C), after which fentanyl and propofol were administered.

For the end purpose at least two signals were continuously acquired from the patients, in this example a pulseplethysmographic (PPG) signal and a facial electro-myographic (FEMG) signal. The instantaneous parameter values of R-to-R interval (=RRIpost and RRIpre), dicrotic notch height (=PtyNotchAmppost and PtyNotch-Amppre), FEMG power (=fEMGpost and fEMGpre) were continuously derived or calculated the heart rate and dicrotic notch being the used quantities. A nonlinear combination of the above parameters according to the invention was calculated, as well as a linear combination of the same parameters as a comparison. The respective instantaneous parameter values were measured real-time or online from each of the patients. The originally received raw signal, i.e. continuous curves of parameter values are not shown in the figures, but the curves normalized with a pre-incision reference level is visualized. Accordingly, FIG. 5A discloses normalized R-to-R interval, FIG. 5B discloses normalized dicrotic notch height, FIG. 5C discloses normalized fEMG power, and FIG. 5D discloses index P for probability of patient comfort obtained by mathematical nonlinear combination of the above mentioned normalized signals. In this mathematical function the ending -post means the latest parameter value and the ending -pre means the calculated historical data of the respective parameter values, which can be also called a reference value. As can be seen there used both subtraction and division between the latest value and the reference value. The time axis is in seconds.

The actual non-linear equation for the mathematical index for probability was:

$$P = \frac{1}{1 + e^{-\left(-8.624\frac{RRIpost}{RRIpre} - 2.672(PtyNotchAmppost - PtyNotchAmppre) + 0.412\frac{fEMGpost}{fEMGpre} + 3.993\right)}}$$

where P is the probability of a movement as a response for noxius stimulus. This index is an indicator for potential nociception during anesthesia or sedation so that a high values of the index indicate high probability for nociception and low values indicate low probability of nociception.

Signs for nociception and inadequate analgesia are clearly seen around intubation (FIG. 5D: arrow B) and incision (FIG. 5D: arrow C) in nonlinear combination parameter but not so clearly in individual variables. Note also recovery from anesthesia (FIG. 5D: arrow D) which is associated with an increase in the index.

The invention claimed is:

1. A method for monitoring a condition of a patient under anesthesia or sedation, the method comprising the steps of:
   acquiring at least a first signal representing a cardiovascular activity of the patent and a second signal representing a combined electrical biopotential obtained from a plurality of biopotential measurements on skull activity of the patient;
   deriving, with a microprocessor, from said first signal, at least a first parameter value;
   calculating, with the microprocessor, from said second signal, at least a second parameter value;
   applying, with the microprocessor, a predetermined mathematical index for probability of patient comfort, in which index said at least first and second parameters are variables;
   calculating, with the microprocessor, successively changing values of said mathematical index; and
   indicating the condition of the patient under anesthesia or sedation with said successive index values.

2. A method according to claim 1, wherein at least first parameter value is related to a quantity selected from a group of quantities including waveform amplitude, waveform periodicity, waveform morphology, and waveform variability.

3. A method according to claim 1, wherein said at least second parameter value is related to a quantity selected from a group of quantities including energy, power, signal complexity and frequency content, each over a predetermined time period.

4. A method according to claim 1, wherein said first signal concerning cardiovascular activity is a blood volume signal measured non-invasively using photoplethysmography.

5. A method according to claim 4, wherein:
   the quantity for said first parameter value is a pulse wave amplitude, or a dicrotic notch height in the pulse wave;
   and calculating from said first signal a third parameter value, the quantity for said third parameter value being a pulse rate, or a heart beat interval, or a temporal position of the dicrotic notch.

6. A method according to claim 1, wherein said second signal is a non-invasive measurement concerning neuromuscular and brain activity.

7. A method according to claim 6, wherein said neuromuscular and brain activity measurement comprises electromyography and electroencephalogram.

8. A method according to claim 7, further comprising the step of extracting electric myographic component from said second signal as an EMG partial signal, and electroencephalographic component as an EEG partial signal.

9. A method according to claim 8, wherein the quantity for said second parameter value is a spectral power calculated from said EMG partial signal.

10. A method according to claim 7, wherein the quantity for said second parameter value is a subtraction of a response entropy, calculated from said second signal as a whole, and a state entropy, calculated from said EEG partial signal.

11. A method according to claim 1, wherein said first signal concerning cardiovascular activity is a cardiac excitation measured non-invasively using electrocardiogram.

12. A method according to claim 11, wherein the quantity for said first parameter value is a heart rate or inter beat interval of the electrical excitation.

13. A method according to claim 1, further comprising the steps of:
    acquiring online a third signal representing a cardiovascular activity of the patient;
    deriving, from said third signal, a fourth parameter value related to a quantity selected from a group of quantities including waveform amplitudes, waveform periodicity, waveform morphology, and waveform variability; and
    introducing said at least fourth parameter in said predetermined mathematical index as an additional variable.

14. A method according to claim 13, wherein the quantity for said first parameter value is a heart rate or inter beat interval of the electrical excitation.

15. A method according to claim 1, wherein said mathematical index for probability is a nonlinear equation.

16. A method according to claim 1, wherein said mathematical index for probability is a neural network algorithm.

17. A method according to claim 1, wherein said mathematical index for probability is based on a defined or fuzzy rule-based reasoning procedure.

18. A method according to claim 1, further comprising the step of normalizing said first and second parameter values on the basis of their respective parameter values acquired over a predetermined fixed time window including or excluding the latest real-time parameter value.

19. A method according to claim 1, wherein said biopotential measurements are selected from electroencephalography, electromyography, and skin conductivity measurements.

20. A method for monitoring a condition of a patient under anesthesia or sedation, the method comprising the steps of:
    acquiring at least a first signal representing a cardiovascular activity of the patient and a second signal representing a combined electrical biopotential obtained by a plurality of biopotential measurements on skull activity of the patient;
    deriving, with a microprocessor, from said first signal, at least a first parameter value;
    calculating, with a microprocessor, from said second signal, at least a second parameter value;
    applying, with a microprocessor, a predetermined mathematical index for probability of patient comfort, in which index said at least first and second parameters are variables;
    calculating, with a microprocessor, successively changing values of said mathematical index;
    indicating the condition of the patient under anesthesia or sedation with said successive index values; and
    normalizing said first and second parameter values on the basis of their respective parameter values acquired over a predetermined fixed time window including or excluding a latest real-time parameter value, wherein said normalized parameter values are acquired from:
        said patient prior to incision, or prior to intubation, or prior to starting anesthesia or sedation, or
        a group of patients prior to or during incision and/or intubation and/or anesthesia or sedation.

* * * * *